US010102638B2

(12) United States Patent
Ito

(10) Patent No.: US 10,102,638 B2
(45) Date of Patent: Oct. 16, 2018

(54) DEVICE AND METHOD FOR IMAGE REGISTRATION, AND A NONTRANSITORY RECORDING MEDIUM

(71) Applicant: FUJIFILM Corporation, Tokyo (JP)

(72) Inventor: Hirotaka Ito, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/423,022

(22) Filed: Feb. 2, 2017

(65) Prior Publication Data

US 2017/0228877 A1 Aug. 10, 2017

(30) Foreign Application Priority Data

Feb. 5, 2016 (JP) .................................. 2016-020359

(51) Int. Cl.
| | |
|---|---|
| *G06K 9/00* | (2006.01) |
| *G06T 7/30* | (2017.01) |
| *G06T 7/00* | (2017.01) |
| *A61B 5/055* | (2006.01) |
| *A61B 6/03* | (2006.01) |

(Continued)

(52) U.S. Cl.
CPC .............. *G06T 7/30* (2017.01); *A61B 5/055* (2013.01); *A61B 6/032* (2013.01); *A61B 6/037* (2013.01); *A61B 6/463* (2013.01); *A61B 6/5229* (2013.01); *G06T 7/0012* (2013.01); *A61B 2090/365* (2016.02); *A61B 2090/374* (2016.02); *A61B 2090/3762* (2016.02); *G06T 2207/10028* (2013.01); *G06T 2207/10081* (2013.01); *G06T 2207/10088* (2013.01); *G06T 2207/10132* (2013.01)

(58) Field of Classification Search
CPC . A61B 2562/08; A61B 5/0008; A61B 5/0084; A61B 5/0538; A61B 5/073
USPC ...... 382/128, 103; 348/222.1, 333.12, 211.8; 340/539.1, 309.16, 540, 573.1; 222/28
See application file for complete search history.

(56) References Cited

U.S. PATENT DOCUMENTS 8,514,067 B2 * 8/2013 Hyde .................... A61B 5/4833
222/28
8,570,391 B2 * 10/2013 Shimamura ........ G06K 9/00228
348/222.1

(Continued)

FOREIGN PATENT DOCUMENTS

| JP | 2010-200894 A | 9/2010 |
|---|---|---|
| JP | 2010-259497 A | 11/2010 |

(Continued)

*Primary Examiner* — Charlotte M Baker
(74) *Attorney, Agent, or Firm* — Birch, Stewart, Kolasch & Birch, LLP

(57) ABSTRACT

A first registration unit performs first registration between a live view and an associated image associated with an object to be imaged. A second registration unit performs second registration between the object captured in the live view and the associated image based on the result of the first registration. At least while the second registration is performed, a display control unit superimposes the associated image on the object captured in the live view, and displays an enlarged view of a partial region of the live view, on which the associated image is superimposed. The second registration unit performs the second registration using a region of the live view larger than the partial region while the enlarged view of the partial region of the live view is displayed.

7 Claims, 5 Drawing Sheets

(51) Int. Cl.
*A61B 6/00* (2006.01)
*A61B 90/00* (2016.01)

(56) References Cited

U.S. PATENT DOCUMENTS

| | | |
|---|---|---|
| 2012/0004557 A1 | 1/2012 | McDowall et al. |
| 2012/0253170 A1 | 10/2012 | Kim et al. |
| 2014/0327792 A1* | 11/2014 | Mulloni .................. G06T 7/73 348/211.8 |
| 2015/0051617 A1 | 2/2015 | Takemura et al. |
| 2016/0089013 A1 | 3/2016 | McDowall et al. |

FOREIGN PATENT DOCUMENTS

| | | |
|---|---|---|
| JP | 2012-205899 A | 10/2012 |
| JP | 2013-531538 A | 8/2013 |
| JP | 2013-202313 A | 10/2013 |

* cited by examiner

DEVICE AND METHOD FOR IMAGE REGISTRATION, AND A NONTRANSITORY RECORDING MEDIUM

CROSS-REFERENCE TO RELATED APPLICATIONS

The present application claims priority under 35 U.S.C. § 119 to Japanese Patent Application No. 2016-020359, filed on Feb. 5, 2016. The above application is hereby expressly incorporated by reference, in its entirety, into the present application.

BACKGROUND

The present disclosure relates to an image registration device, an image registration method, and an image registration program for performing registration between an object captured in a live view and an associated image associated with the object.

In recent years, surgery simulation using three-dimensional medical images is becoming popular. The surgery simulation refers to simulation of an actual surgical procedure with visualizing a tissue or an organ, which is the objects of the surgery, and surrounding structures thereof from medical images. For example, with simulation of partial resection of the liver, tissues, such as the liver, the portal vein, veins, arteries, the body surface, bones, and a tumor, are extracted from a tomographic image, such as a CT (Computed Tomography) image or an MRI (Magnetic Resonance Imaging) image, and a three-dimensional image visualizing the extracted tissues is generated. This images is used to make a surgical plan by, for example, calculating, with a computer, an area to be resected of the liver region including, for example, a tumor in the liver.

On the other hand, there is a demand for viewing such an image used for the surgery simulation (which will hereinafter be referred to as "simulation image"), as described above, as a reference during surgery. For this reason, such a simulation image may be printed on paper and brought in the surgery room, or may be displayed on a display device installed in the surgery room. Then, the surgeon conducts the surgery with looking at the actual surgical site of the patient, and the simulation image printed on paper or displayed on the display device for confirmation.

It is, however, very troublesome to conduct surgery with alternately looking at the patient and the simulation image, and there is a demand for displaying a simulation image superimposed on an image of the actual object of the surgery. To meet this demand, some approaches have been proposed for obtaining a live view formed by a plurality of images by imaging the surgical site during surgery, and displaying a simulation image superimposed on the live view. For example, Japanese Unexamined Patent Publication No. 2013-202313 (hereinafter, Patent Document 1) proposes an approach which involves attaching an optical sensor or a magnetic sensor to a camera for imaging the surgical site, to a surgical tool, or directly to an organ and performing calibration, i.e., initial registration of the relative positional relationship among them, and moving a simulation image relative to change of the position and orientation of the camera and movement of the organ after the initial registration, to thereby display the simulation image that is registered with and superimposed on the view of the surgical site.

Also, an approach which involves placing a marker on a surgical site, detecting the position of the marker with a sensor to register a simulation image with the surgical site, and displaying the simulation image on a head-mount display (see Japanese Unexamined Patent Publication No. 2010-259497 (hereinafter, Patent Document 2)), and an approach which involves embedding a marker in a surgical site, detecting the marker with a sensor to register a simulation image with the surgical site, and displaying the simulation image registered with the surgical site on a monitor (see Japanese Unexamined Patent Publication No. 2010-200894 (hereinafter, Patent Document 3)) have been proposed.

On the other hand, approaches where registration between an image of a patient obtained by imaging and a simulation image is performed without using a sensor, or the like, have been proposed. For example, Japanese Unexamined Patent Publication No. 2012-205899 (hereinafter, Patent Document 4) proposes an approach which involves generating a model of an organ from a three-dimensional image, and calculating an affine transformation function between the model of the organ and each frame of an ultrasonic image to display the model of the organ superimposed on the ultrasonic image real-time, and superimposing the model of the organ on the ultrasonic image by transforming the model of the organ based on the affine transformation function.

Further, in order to facilitate viewing the obtained image, the image is displayed with being enlarged. For example, PCT Japanese Publication No. 2013-531538 (hereinafter, Patent Document 5) proposes an approach where a surgery system displays an enlarged image of a fluorescent image, which is simultaneously obtained with a monochrome image, superimposed on the monochrome image.

SUMMARY

When an associated image associated with an object being imaged is displayed with being superimposed on a live view capturing the object, such as when a simulation image is displayed with being superimposed on the live view, as described above, displaying an enlarged image of the objective site in the live view and the associated image facilitates seeing the objective site. However, when the live view and the associated image are enlarged, the enlarged live view includes less information necessary for the registration. With less information necessary for the registration, it is difficult to achieve accurate registration between the live view and the associated image.

In view of the above-described circumstances, the present disclosure is directed to facilitating viewing a live view with an associated image that is associated with an object being imaged superimposed thereon, and achieving accurate registration between the associated image and the live view.

An aspect of an image registration device according to the disclosure comprises:

an image obtaining unit configured to obtain a live view comprising two or more images taken at different times, the live view capturing an object to be imaged;

an associated image obtaining unit configured to obtain an associated image associated with the object;

a display control unit configured to display the live view and the associated image on a display unit;

a first registration unit configured to perform, according to a first registration instruction, first registration between the object captured in the live view and the associated image; and a second registration unit configured to perform second registration between the object captured in the live view and the associated image based on the result of the first registration, wherein, at least while the second registration is performed, the display control unit superimposes the associated image on the object captured in the live view, and displays an enlarged view of a partial region of the live view, on which the associated image is superimposed, on the display unit, and the second registration unit performs the second registration using a region of the live view larger than the partial region while the enlarged view of the partial region of the live view is displayed.

The term "associated image" as used herein refers to any image associated with an object captured in the live view. Examples of an image usable as the associated image include an image representing the three-dimensional shape of the object generated from a CT image or an MRI image, an image representing the three-dimensional shapes of the object and structures included in the object generated from a CT image or an MRI image, a symbol, such as a line or an arrow, indicating a resection position of the object determined on an image representing the three-dimensional shape of a structure (i.e., a surgery simulation image), or image information, such as a functional three-dimensional image obtained through PET (Positron Emission Tomography) scanning or NM (Nuclear Medical) scanning. Further, an image of text information representing the names of the object and structures included in the object to be displayed on the display unit is also considered as an image and is usable as the associated image.

The term "first registration instruction" as used herein refers to instructions to change at least one of translation, rotation, scaling, and orientation of the associated image to register the associated image with the object captured in the live view. It should be noted that "changing the orientation" refers to rotating the associated image about an axis that is parallel to or along the display surface of the display unit. On the other hand, the "rotation" refers to rotation about an axis that is perpendicular to the display surface of the display unit.

The description "at least while the second registration is performed" as used herein may mean not only while the second registration is performed but also while the first registration is performed.

The description "a region larger than the partial region" means a region that is larger than the partial region and is not necessarily include the partial region.

The image registration device according to the disclosure may further comprise an input unit configured to receive specification of the partial region.

In this case, the display control unit may extract the specified partial region from the live view, and enlarge only the extracted partial region to display an enlarged view of the extracted partial region on the display unit.

The image obtaining unit performs imaging so as to capture the object. However, the imaged area may be shifted during imaging. The description "extracts the specified partial region from the live view" means extracting a region corresponding to the partial region from sequentially obtained images forming the live view, so that the same image as the specified partial region is enlarged and displayed on the display unit even when the imaged area is shifted.

In the image registration device according to the disclosure, the second registration unit may perform the second registration using the entire region of the live view while the enlarged view of the partial region of the live view is displayed.

In the image registration device according to the disclosure, if the object includes at least one structure, the associated image may be an image representing three-dimensional shapes of the object and the at least one structure.

An aspect of an image registration method according to the disclosure comprises the steps of:

obtaining a live view comprising two or more images taken at different times, the live view capturing an object to be imaged;

obtaining an associated image associated with the object;

displaying the live view and the associated image on a display unit;

performing, according to a first registration instruction, first registration between the object captured in the live view and the associated image;

performing second registration between the object captured in the live view and the associated image based on the result of the first registration;

superimposing the associated image on the object captured in the live view, and displaying an enlarged view of a partial region of the live view, on which the associated image is superimposed, on the display unit at least while the second registration is performed; and performing the second registration using a region of the live view larger than the partial region while the enlarged view of the partial region of the live view is displayed.

It should be noted that the image registration method according to the disclosure may be provided in the form of a program for causing a computer to execute the image registration method.

According to the disclosure, a live view and an associated image superimposed on the live view are displayed on a display unit, and first registration between an object captured in the live view and the associated image is performed. After the first registration, second registration between the associated image and the object captured in the live view is performed based on the result of the first registration. At least while the second registration is performed, the associated image is superimposed on the object captured in the live view, and an enlarged view of a partial region of the live view, on which the associated image is superimposed, is displayed. Further, the second registration is performed using a region of the live view larger than the partial region while the enlarged view of the partial region of the live view is displayed. Displaying the enlarged view of the partial region in this manner facilities viewing the live view with the associated image being superimposed thereon. Further, since the second registration is performed using a region larger than the partial region, there is more information necessary for the registration than the case where the registration is performed using only the partial region, and this allows the second registration to be achieved accurately.

DETAILED DESCRIPTION OF THE PREFERRED EMBODIMENTS

Figure 1:
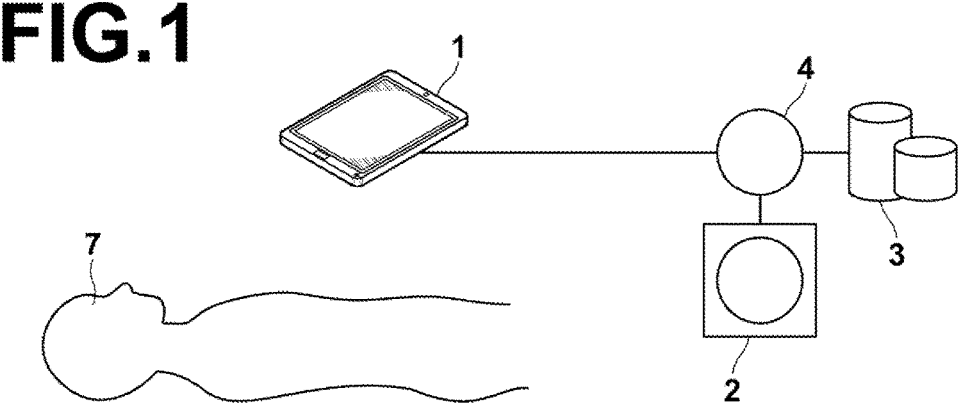
FIG. 1 is a diagram illustrating the hardware configuration showing the outline of a surgery assisting system to which an image registration device according to an embodiment of the disclosure is applied.

Hereinafter, an embodiment of the present disclosure will be described with reference to the drawings. FIG. 1 is a diagram illustrating the hardware configuration showing the outline of a surgery assisting system to which an image registration device according to an embodiment of the disclosure is applied. As shown in FIG. 1, in this system, an image registration device 1 according to this embodiment, a three-dimensional imaging apparatus 2, and an image repository server 3 are connected to one another via a network 4 such that they can communicate with one another.

The three-dimensional imaging apparatus 2 images a surgical site of a subject 7 to generate a three-dimensional image V0 representing the surgical site, and specific examples thereof include a CT apparatus, an MRI apparatus, and a PET apparatus. The three-dimensional image V0 generated by the three-dimensional imaging apparatus 2 is sent to and stored in the image repository server 3. It should be noted that, in this embodiment, it is assumed that the surgical site of the subject 7 is the liver, the three-dimensional imaging apparatus 2 is a CT apparatus, and the three-dimensional image V0 of the abdomen of the subject 7 is generated.

The image repository server 3 is a computer that stores and manages various data, and includes a high-capacity external storage device and a database management software. The image repository server 3 communicates with the other components of the system via the network 4, which is a wired or wireless network, to send and receive image data, etc. Specifically, the image data, such as the three-dimensional image V0 generated by the three-dimensional imaging apparatus 2, is obtained via the network, and is stored and managed in a storage medium, such as the high-capacity external storage device. It should be noted that the format of the stored image data and communication among the components of the system via the network 4 are based on a protocol, such as DICOM (Digital Imaging and COmmunication in Medicine).

The image registration device 1 is implemented by installing an image registration program of the disclosure on a single computer. In this embodiment, the computer is a tablet terminal that is wirelessly connected to the network 4 and is directly operated by the surgeon, who is the operator of the image registration device. The image registration program is distributed with being recorded on a storage medium, such as a DVD (Digital Versatile Disc) or CD-ROM (Compact Disc Read Only Memory), and is installed on the tablet terminal from the storage medium. Alternatively, the image registration program may be stored in a storage device of a server computer connected to the network, or a network storage, such that it is externally accessible, and may be download and installed on the tablet terminal per request.

Figure 2:
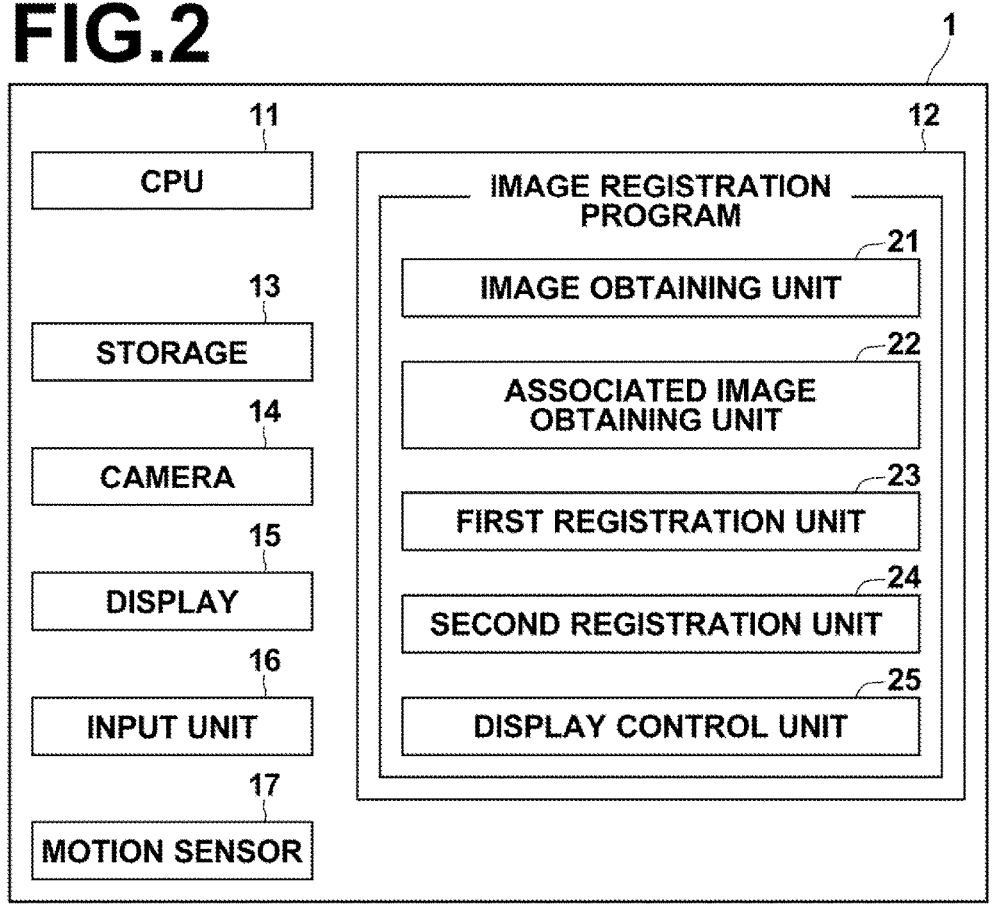
FIG. 2 is a diagram illustrating the schematic configuration of the image registration device implemented by installing an image registration program on a tablet terminal.

FIG. 2 is a diagram illustrating the schematic configuration of the image registration device implemented by installing the image registration program on the tablet terminal. As shown in FIG. 2, the image registration device 1 includes, as the configuration of a standard tablet terminal, a CPU (Central Processing Unit) 11, a memory 12, a storage 13, a camera 14, a display 15, such as a liquid crystal display, a touch-panel input unit 16, and a motion sensor 17.

The storage 13 stores the three-dimensional image V0 obtained from the image repository server 3 via the network 4, and various information including images generated by operation of the image registration device 1.

The camera 14 includes a lens, an image sensor, such as a CCD (Charge Coupled Device), and an image processing unit, etc., for processing the obtained image to improve the image quality. The surgeon images the liver, which is the surgical site of the subject 7 undergoing surgery, of the subject 7 having been subjected to laparotomy using the camera 14 of the image registration device 1, i.e., the tablet terminal, to obtain an intraoperative live view L0, which is formed by two or more images taken at different times, capturing the liver during the surgery. It should be noted that, in this embodiment, the liver corresponds to the object to be imaged. The intraoperative live view L0 is a moving image formed by sequential intraoperative images at a predetermined frame rate, such as 30 fps.

The motion sensor 17 is a nine-axis motion sensor that detects acceleration along three axes, i.e., the x-axis, the y-axis, and the z-axis, angular speed along the three axes, and inclination along the three axes relative to the position of the tablet terminal. Thus, the motion sensor 17 detects movement of the tablet terminal, i.e., movement of the camera 14. The acceleration, the angular speed, and the inclination detected by the motion sensor 17 are outputted as movement information to the CPU 11 and are used as necessary.

The memory 12 stores the image registration program. The image registration program prescribes, as operations to be executed by the CPU 11: an image obtaining operation to obtain the intraoperative live view L0 capturing the liver, which is the object to be imaged, and the three-dimensional image V0; an associated image obtaining operation to obtain an associated image S0 associated with the liver, which is the object captured in the intraoperative live view L0; a first registration operation to perform first registration, which is the initial registration, between the liver captured in the intraoperative live view L0 and the associated image S0; a second registration operation to perform registration between the liver captured in the intraoperative live view L0 and the associated image S0; and a display control operation to superimpose the associated image S0 on the liver captured in the intraoperative live view L0, and display an enlarged view of a partial region of the intraoperative live view L0, on which the associated image S0 is superimposed, on the display 15 at least while the second registration is performed. It should be noted that the second registration operation performs the second registration using a region of the intraoperative live view L0 larger than the partial region while the enlarged view of the partial region of the intraoperative live view L0 is displayed.

When the CPU 11 executes these operations according to the program, the tablet terminal functions as an image obtaining unit 21, an associated image obtaining unit 22, a first registration unit 23, a second registration unit 24, and a display control unit 25. It should be noted that the image registration device 1 may include different processors for executing the image obtaining operation, the associated image obtaining operation, the first registration operation, the second registration operation, and the display control operation, respectively.

The image obtaining unit 21 obtains the three-dimensional image V0, and the intraoperative live view L0 capturing the objective site of the subject 7 undergoing surgery, which is imaged with the camera 14. In the case where the three-dimensional image V0 has already been stored in the storage 13, the image obtaining unit 21 may obtain the three-dimensional image V0 from the storage 13. It should be noted that, in this embodiment, the intraoperative live view L0 is obtained by the surgeon by imaging, from above, the liver of the subject 7 having been subjected to laparotomy.

The associated image obtaining unit 22 generates a surgery simulation image of the liver as the associated image S0. For this purpose, the associated image obtaining unit 22 first extracts, from the three-dimensional image V0, the liver, and the hepatic artery, the hepatic vein, and a lesion included in the liver. The associated image obtaining unit 22 includes a classifier for classifying each pixel of the three-dimensional image V0 into pixels representing the liver, and the artery, the vein, and the lesion included in the liver (which will hereinafter be referred to as "the liver, and the like") and other pixels. The classifier is obtained through machine learning using a plurality of sample images of the liver, and the like, based on a technique, such as the Ada-Boosting algorithm. The associated image obtaining unit 22 extracts the liver, and the like, from the three-dimensional image V0 using the classifier.

Then, the associated image obtaining unit 22 generates an image representing the three-dimensional shapes of the liver, and the like, as the associated image S0. Specifically, a projection image of the extracted liver, and the like, projected on a predetermined projection plane is generated as the associated image S0. The projection plane may, for example, be a plane directly facing the liver of the subject 7. It should be noted that, as a specific projection method, a known technique, such as volume rendering, is used.

Figure 3:
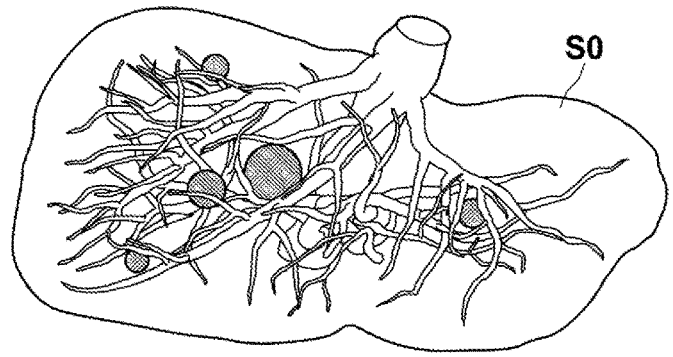
FIG. 3 is a diagram illustrating one example of an associated image.

At this time, the associated image S0 may be generated with defining different colors or different transparency values for the liver, and the hepatic artery, the hepatic vein, and the lesion included in the liver. For example, the hepatic artery may be shown in red, the hepatic vein may be shown in blue, and the lesion may be shown in green, and/or the liver may be shown with an opacity value of 0.1, the hepatic artery and the hepatic vein may be shown with an opacity value of 0.5, and the lesion may be shown with an opacity value of 0.8. In this manner, the associated image S0, as shown in FIG. 3, is generated. Defining different colors or different transparency values for the liver, and the hepatic artery, the hepatic vein, and the lesion included in the liver in the associated image S0 facilitates identifying the liver, and the hepatic artery, the hepatic vein, and the lesion included in the liver. It should be noted that both different colors and different transparency values may be defined to generate the associated image S0. The thus generated associated image S0 is stored in the storage 13.

Now, a process performed in this embodiment is described along with description of the first and second registration units 23, 24, and the display control unit 25.

Figure 4:
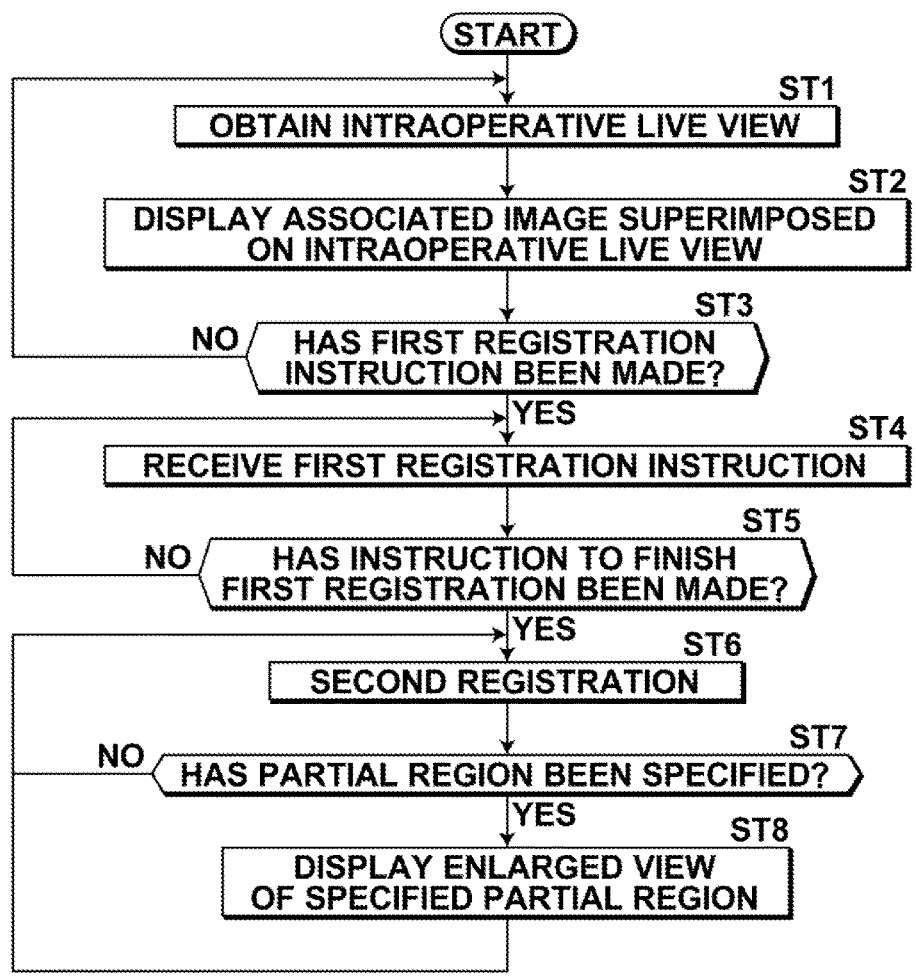
FIG. 4 is a flow chart showing a process performed in an embodiment of the disclosure.

FIG. 4 is a flow chart showing the process performed in this embodiment. It is assumed that the associated image S0 has already been generated and stored in the storage 13. First, the liver of the subject 7 is imaged to obtain the intraoperative live view L0 (step ST1). Then, the display control unit 25 displays, on the display 15, the associated image S0 superimposed on the intraoperative live view L0 (step ST2). It should be noted that, at this stage, the associated image S0 is displayed at a predetermined position on the display 15.

Subsequently, the first registration unit 23 begins monitoring to determine whether or not a first registration instruction has been made (step ST3). If the determination in step ST3 is affirmative, the first registration unit 23 receives the first registration instruction made by the surgeon (step ST4). In response to the first registration instruction, the first registration unit 23 performs the first registration, which is the initial registration.

Figure 5:
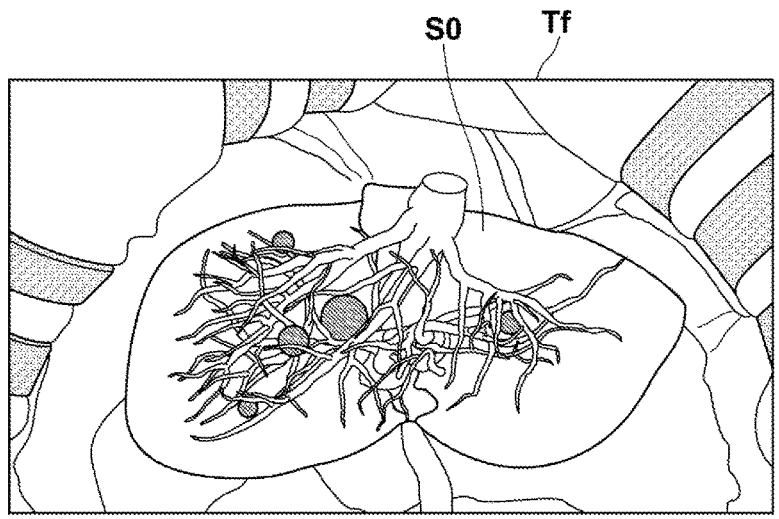
FIG. 5 is a diagram illustrating an initial intraoperative image that is displayed on a display device during first registration.

FIG. 5 is a diagram illustrating an image displayed on the display 15 during the first registration. The associated image S0, which is displayed as described above, is ready for translation, rotation, and scaling according to operation of the input unit 16, i.e., touch operation made on the display 15. Assuming that the x-axis and the y-axis are set along the display surface of the display 15 and the z-axis is set along the direction perpendicular to the display surface, rotation can be performed in any direction about the three axes. It should be noted that the rotation as used herein refers to rotation about the z-axis. When the associated image S0 is rotated about an axis other than the z-axis, i.e., is rotated about the x-axis and/or the y-axis, the orientation of the associated image S0 is changed. The rotation of the associated image S0 about the x-axis and/or y-axis is defined herein as change of the orientation.

When the orientation of the associated image S0 is changed, the projection plane of the associated image S0 is changed. Accordingly, when the orientation of the associated image S0 is changed and the projection plane is changed, the associated image obtaining unit 22 generates the associated image S0 again.

The surgeon performs translation, rotation, and scaling of the associated image S0 while viewing the intraoperative live view L0 and the associated image S0 displayed on the display 15 such that the position of the associated image is aligned with the position of the liver captured in the intraoperative live view L0. Further, the surgeon may change the orientation of the associated image S0, if necessary. At this time, the transparency of the associated image S0 may also be changed. The transparency of the associated image S0 may be changed in response to an instruction inputted via the input unit 16, or the transparency may be changed when the surgeon makes touch operation on the display 15 for the first registration.

Then, when alignment between the position of the associated image S0 and the position of the liver captured in the intraoperative live view L0 is achieved, an instruction to finish the first registration is made via the input unit 16, and the first registration ends. It should be noted that the instruction to finish the first registration may be made via a button displayed on the display 15 to be operated via the input unit 16, or by making a predetermined operation, such as double tap. Then, an intraoperative image which is one frame of the intraoperative live view L0 displayed on the display 151 at the end of the first registration is stored as an initial intraoperative image Tf in the storage 13.

It should be noted that, in this embodiment, the surgical site is the liver, and the liver may possibly be resected and moved during the surgery. For this reason, in this embodiment, the initial intraoperative image Tf, which is one frame of the intraoperative live view L0, is kept displayed on the display 15 at the end of the first registration for receiving specification of unchanged positions that are not changed during the surgery. For example, in the initial intraoperative image Tf shown in FIG. 6, a site where a surgical tool, such as forceps 30, is present is not moved during the surgery. Further, in a case where the left lobe of the liver is resected, the right lobe of the liver is not moved during the surgery. Accordingly, in this embodiment, specification of unchanged positions that are not moved during the surgery, such as a position O1 on the edge of the forceps 30 or a position O2 on the right lobe of the liver, is received via the input unit 16 and the specified unchanged positions are stored in the storage 13.

Then, the first registration unit 23 determines whether or not an instruction to finish the first registration has been made (step ST5). It should be noted that the operation in step ST5 may be performed by the second registration unit 24. If the determination in step ST5 is negative, the process returns to step ST4, and reception of the first registration instruction is continued. If the determination in step ST5 is affirmative, the second registration unit 24 performs second registration (step ST6).

Figure 7:
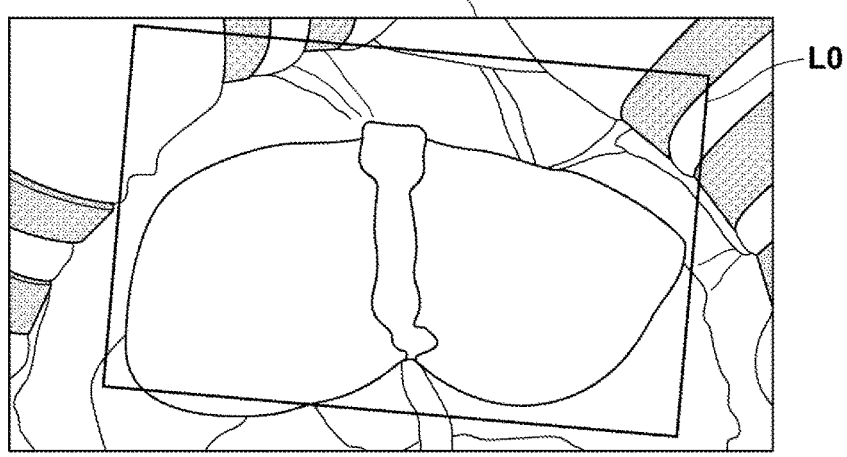
FIG. 7 is a diagram for explaining positional difference of a currently displayed intraoperative image relative to the initial intraoperative image.

After the first registration, the surgeon proceeds with the surgery. During the surgery, the surgeon cannot always hold the tablet terminal above the subject 7, and imaging of the objective site with the tablet terminal is temporarily stopped. Thereafter, imaging of the liver, which is the object, with the tablet terminal is performed when it is necessary, such as for confirming the position of the lesion. At this time, imaging of the liver is performed again with the position of the tablet terminal being moved from the position where the first registration has been performed. In such a situation, the position of the camera 14 is different from the position thereof where the initial intraoperative image Tf has been taken, and the position of the intraoperative live view L0 displayed on the display 15 is different from the position of the initial intraoperative image Tf, as shown in FIG. 7. Further, even in a case where the tablet terminal is held above the subject 7, the tablet terminal is moved as long as it is held by a hand, and the position of the intraoperative live view L0 displayed on the display 15 is shifted from the position of the initial intraoperative image Tf.

The second registration unit 24 obtains, based on the above-described unchanged positions, positional information that indicates a relative positional difference between the initial intraoperative image Tf and an intraoperative image (which is designated by T1) that forms the intraoperative live view L0 and is obtained after the first registration. It should be noted that the intraoperative image T1 may be obtained just after the first registration, or may be obtained some time later from the end of the first registration, as long as there is no problem with observation of the state where the associated image S0 is displayed with being superimposed on the liver captured in the intraoperative live view L0.

Figure 6:
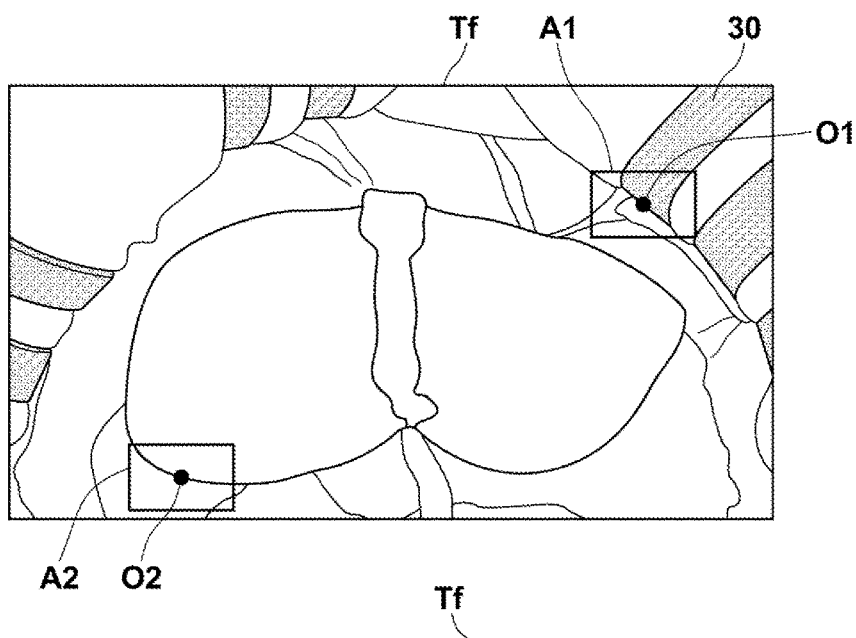
FIG. 6 is a diagram for explaining how each region with an unchanged position being the center is set.

The second registration unit 24 first performs template matching between the intraoperative image T1 and the initial intraoperative image Tf using the unchanged positions as the reference points to obtain the positional information. A technique usable to achieve the template matching includes: setting regions A1, A2 with the unchanged positions O1, O2 being the center, respectively, as shown in FIG. 6, on the initial intraoperative image Tf; and calculating, based on correspondence relationship between the regions A1, A2 and the intraoperative image T1, at least one of a translational component, a rotational component, and a scaling factor of the intraoperative image T1 relative to the initial intraoperative image Tf as the positional information. It should be noted that the rotation as used herein refers to two-dimensional rotation about the z-axis (i.e., in the xy-plane).

The positional information indicates a relative positional difference of the currently displayed intraoperative image T1 relative to the initial intraoperative image Tf. That is, the positional information corresponds to a relative positional difference between the current position of the camera 14 and the position of the camera 14 during the first registration.

Figure 8:
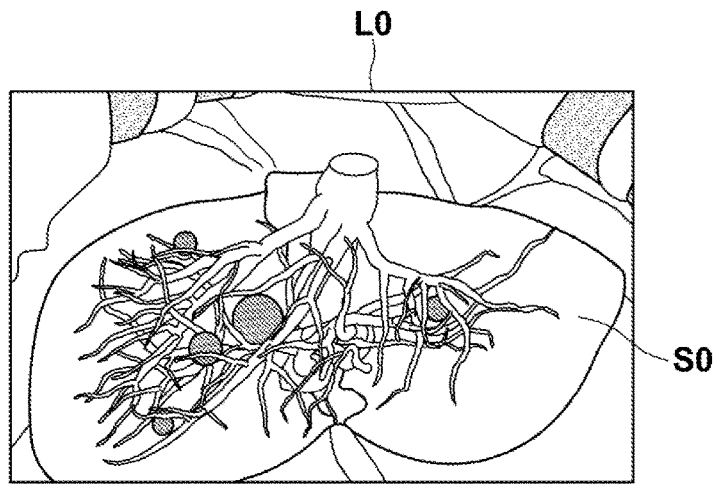
FIG. 8 is a diagram for explaining how an associated image is displayed with being superimposed on the intraoperative live view.

The second registration unit 24 performs registration between the initial intraoperative image Tf and the intraoperative image T1 using the positional information, and uses the result of this registration to perform the second registration. That is, the associated image S0 is displayed with being superimposed on the registered intraoperative image T1. At this time, the associated image S0 is subjected to translation, rotation, and/or scaling based on the positional information. In this manner, as shown in FIG. 8, the associated image S0 is displayed with being superimposed on the intraoperative live view L0 at the same position as the position registered with the initial intraoperative image Tf.

Subsequently, the display control unit 25 determines whether or not a partial region of the intraoperative live view L0 has been specified by the surgeon (step ST7). If the determination in step ST7 is negative, the process returns to step ST6, and the second registration is continued. If the determination in step ST6 is affirmative, the display control unit 25 displays an enlarged view of the specified partial region on the display 15 (step ST8), and the process returns to step ST6.

Figure 9:
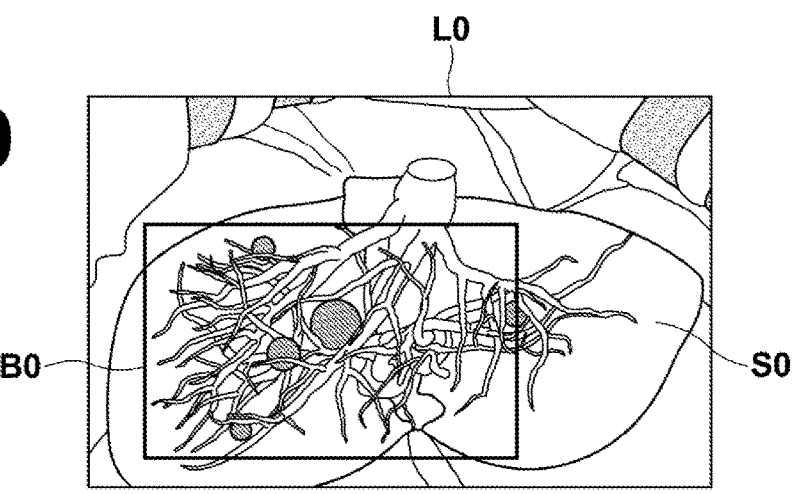
FIG. 9 is a diagram for explaining how a partial region is specified.
Figure 10:
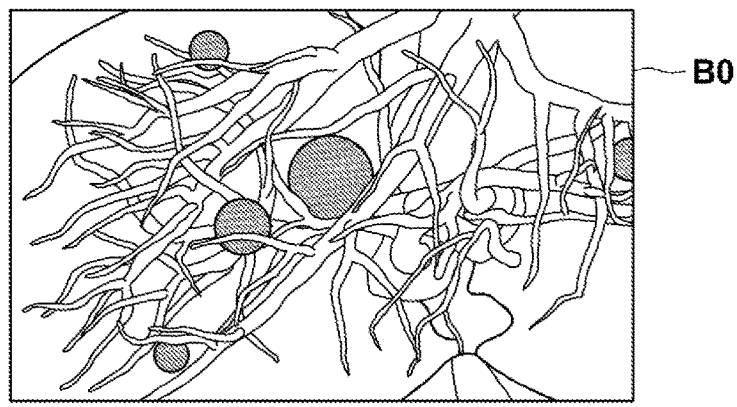
FIG. 10 is a diagram illustrating an enlarged view of the partial region displayed on the display device.

FIG. 9 is a diagram for explaining specification of the partial region. As shown in FIG. 9, the surgeon specifies a partial region B0, which the surgeon wants to enlarge, of the intraoperative live view L0 on which the associated image S0 is superimposed. It should be noted that specification of the partial region B0 is achieved by inputting an instruction specifying the region on the display 15 via the input unit 16. Specifically, specification of the partial region B0 is achieved, for example, by tracing, with a finger, a rectangular region or opposite ends of a diagonal line of the rectangular region on the display 15. Then, the display control unit 25 extracts the partial region B0 from the intraoperative live view L0, and displays an enlarge view of the partial region B0 on the display 15, as shown in FIG. 10.

It may be contemplated that the second registration may be performed using the partial region B0 that is displayed with being enlarged. The partial region B0, however, does not include the unchanged positions captured in the initial intraoperative image Tf, or includes an insufficient number of the unchanged positions for the registration. Using the partial region B0 to perform the second registration would fail to achieve accurate registration. In this embodiment, the second registration after the enlarged view of the partial region B0 is displayed is performed using a region larger than the partial region B0 of the intraoperative live view L0. The region larger than the partial region B0 may be, but not limited to, the entire intraoperative live view L0. Further, the region larger than the partial region B0 may include the entire partial region B0, a part of the partial region B0, or no partial region B0.

As described above, in this embodiment, the second registration is performed using a region larger than the partial region B0 of the intraoperative live view L0 while the enlarged image of the partial region B0 is displayed. Displaying the enlarge view of the partial region B0 facilitates viewing the intraoperative live view L0 with the associated image S0 superimposed thereon. Further, since the second registration is performed using a region larger than the partial region B0, more information necessary for the registration can be provided than in the case where only the partial region B0 is used for the registration, and the second registration can be accurately achieved.

In a case where the tablet terminal is held above the subject 7, the tablet terminal is moved as long as it is held by a hand, and the position of the intraoperative live view L0 displayed on the display 15 is shifted from the position of the initial intraoperative image Tf. In this case, the enlarged view of the partial region B0 being displayed may also be moved according to the movement of the tablet terminal. Alternatively, a region corresponding to the specified partial region B0 may be extracted from the sequentially obtained intraoperative live view L0, and the enlarged view of the partial region B0 displayed on the display 15 may not be moved when the tablet terminal is moved. This allows preventing blur or shaking of the partial region B0 being displayed due to camera shake, etc., which may otherwise make it difficult to view the partial region B0.

Although an enlarged view of the partial region is displayed during the second registration in the above-described embodiment, specification of a partial region may be received during the first registration and an enlarged view of the specified partial region may be displayed during the first registration.

Figure 11:
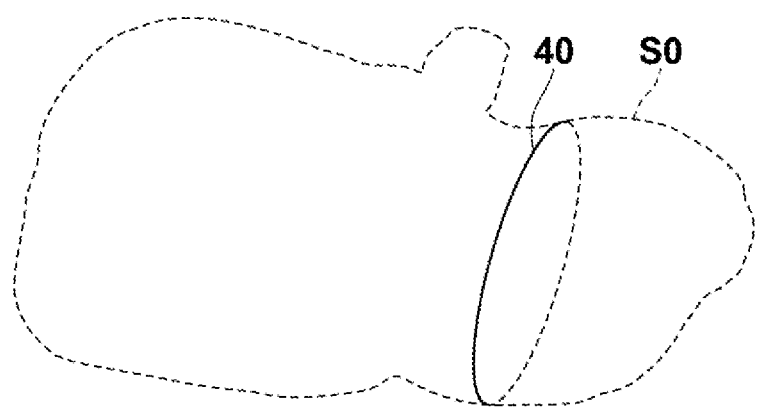
FIG. 11 is a diagram illustrating another example of the associated image.

Further, although a projection image of the liver extracted from the three-dimensional image V0 generated by a modality, such as a CT apparatus, is used as the associated image S0 in the above-described embodiment, this is not intended to limit the disclosure, and a functional three-dimensional image which is obtained through PET scanning or nuclear medicine scanning may be used as the associated image. The associated image S0 is not limited to image information, and a simulation image S0 including a line indicating a resection position, i.e., a resection line 40, as shown in FIG. 11, a symbol, such as an arrow, or text information, such as the names of sites and tissues around the resection position, may be used as the associated image S0. Also, a combination of image information, symbols, and/or text information may be used as the associated image.

Still further, although specification of the partial region B0 by the surgeon is received in the above-described embodiment, a region including a lesion in the liver captured in the intraoperative live view L0, or a region of the associated image S0 including a resection line for the surgery, for example, may be automatically extracted as the partial region B0, and an enlarged view of the extracted partial region B0 may be displayed.

In the above-described embodiment, the motion sensor 17 may detect movement of the tablet terminal, i.e., the camera 14, and the detected movement may be used to perform the second registration. In this case, the movement of the tablet terminal, i.e., the camera 14, detected by the motion sensor 17 may be a movement of the camera from the position at the beginning of the first registration to the current position of the camera during the second registration, or a movement between a currently obtained intraoperative image and a previously obtained intraoperative image. In the former case, the movement detected by the motion sensor 17 represents an amount of translation, an amount of rotation, and an amount of scaling between the current intraoperative image and the initial intraoperative image Tf. Accordingly, the associated image S0 registered during the first registration is further subjected to translation, rotation, and scaling based on the movement detected by the motion sensor 17, and is superimposed on the intraoperative live view L0 to achieve the second registration. In the latter case, the associated image S0 registered during the previous second registration is further subjected to translation, rotation, and scaling based on the movement detected by the motion sensor 17, and is superimposed on the intraoperative live view L0 to achieve the second registration.

Although the initial intraoperative image Tf is displayed on the display 15 and the first registration of the associated image S0 is performed manually by the operator in the above-described embodiment, the initial registration between the associated image S0 and the liver captured in the initial intraoperative image Tf may be automatically performed. In this case, the initial intraoperative image Tf, which is a still image, is used, and this allows quickly achieving the first registration.

Further, although the associated image S0 is used during the first registration in the above-described embodiment, only the contour of the liver included in the associated image S0 may be extracted as a boundary image, and the boundary image may be used to perform the first registration.

Still further, although the associated image S0 is displayed on the tablet terminal with being superimposed on the intraoperative live view L0 in the above-described embodiment, the disclosure is also applicable to registration of the associated image S0 in a case where the intraoperative live view L0 is displayed on a head-mount display. The disclosure is also applicable to registration of the associated image S0 in case where the intraoperative live view L0 is taken with a camera disposed above the surgical table, and the taken image is displayed on a display device inside or outside the surgery room. In this case, the image registration device 1 according to this embodiment is installed on a computer, and registration between the intraoperative live view L0 and the associated image S0 is performed on the computer. Then, the intraoperative live view L0 and the associated image S0 superimposed thereon are displayed on the head-mount display or the display device connected to the computer. In this case, specification of the partial region B0 may be performed with viewing the intraoperative live view displayed on the head-mount display, or the like.

Although the associated image S0 is generated by the associated image obtaining unit 22 in the above-described embodiment, the associated image S0 may be generated by an associated image obtaining unit that is provided separately from the image registration device 1. In this case, the associated image obtaining unit 22 need not be capable of generating the associated image S0, and the configuration of the image registration device 1 can be simplified.

Although the first registration is performed by changing translation, rotation, scaling, and orientation of the associated image S0 in the above-described embodiment, associated images oriented in various directions may be prepared in advance, and the first registration may be performed with selecting one of the associated images with an orientation that most matches the orientation of the objective site captured in the intraoperative live view L0 during the first registration.

Although the hepatic artery, etc., included in the liver are extracted and included in the associated image S0 in the above-described embodiment, only the liver, which is the surgical site, may be extracted, and an image representing only the three-dimensional shape of the liver may be used as the associated image S0.

Although the liver is used as the object in the above-described embodiment, this is not intended to limit the disclosure, and the disclosure is applicable to any surgical site in the case where the associated image S0 is displayed with being superimposed on the intraoperative live view L0.

Although the object is a surgical site of a human body in the above-described embodiment, the disclosure is also applicable to a case where registration between an object captured in a live view of a non-human subject and an associated image S0 associated with the object is performed.

Now, advantageous effects of the embodiments of the disclosure are described.

Receiving specification of a partial region allows displaying an enlarged view of the partial region desired by the user.

In the case where only the specified partial region is enlarged and displayed, the partial region being displayed during imaging is not changed, and this allows preventing blur or shaking of the image being displayed due to camera shake, etc., which may otherwise make it difficult to view the displayed image.

What is claimed is:

1. An image registration device comprising:
   an image obtaining unit configured to obtain a live view comprising two or more images taken at different times, the live view capturing an object to be imaged;
   an associated image obtaining unit configured to obtain an associated image associated with the object;
   a display control unit configured to display the live view and the associated image on a display unit;
   a first registration unit configured to perform, according to a first registration instruction, first registration between the object captured in the live view and the associated image; and
   a second registration unit configured to perform second registration between the object captured in the live view and the associated image based on the result of the first registration,
   wherein, at least while the second registration is performed, the display control unit superimposes the associated image on the object captured in the live view to achieve a registration between the associated image and the live view, and displays an enlarged view of a partial region of the live view, on which the associated image is superimposed, on the display unit, and
   the second registration unit performs the second registration using a region of the live view larger than the partial region while the enlarged view of the partial region of the live view is displayed.

2. The image registration device as claimed in claim 1 further comprising an input unit configured to receive specification of the partial region.

3. The image registration device as claimed in claim 2, wherein the display control unit extracts the specified partial region from the live view, and enlarges only the extracted partial region to display an enlarged view of the extracted partial region on the display unit.

4. The image registration device as claimed in claim 1, wherein the second registration unit performs the second registration using the entire region of the live view while the enlarged view of the partial region of the live view is displayed.

5. The image registration device as claimed in claim 1, wherein, if the object includes at least one structure, the associated image is an image representing three-dimensional shapes of the object and the at least one structure.

6. An image registration method comprising the steps of:
   obtaining a live view comprising two or more images taken at different times, the live view capturing an object to be imaged;
   obtaining an associated image associated with the object;
   displaying the live view and the associated image on a display unit;
   performing, according to a first registration instruction, first registration between the object captured in the live view and the associated image;
   performing second registration between the object captured in the live view and the associated image based on the result of the first registration;
   superimposing the associated image on the object captured in the live view to achieve a registration between the associated image and the live view, and displaying an enlarged view of a partial region of the live view, on which the associated image is superimposed, on the display unit at least while the second registration is performed; and
   performing the second registration using a region of the live view larger than the partial region while the enlarged view of the partial region of the live view is displayed.

7. A non-transitory recording medium with an image registration program recorded thereon, the image registration program causing a computer to execute the steps of:
   obtaining a live view comprising two or more images taken at different times, the live view capturing an object to be imaged;
   obtaining an associated image associated with the object;
   displaying the live view and the associated image on a display unit;
   performing, according to a first registration instruction, first registration between the object captured in the live view and the associated image;
   performing second registration between the object captured in the live view and the associated image based on the result of the first registration;
   superimposing the associated image on the object captured in the live view to achieve a registration between the associated image and the live view, and displaying an enlarged view of a partial region of the live view, on which the associated image is superimposed, on the display unit at least while the second registration is performed; and
   performing the second registration using a region of the live view larger than the partial region while the enlarged view of the partial region of the live view is displayed.

* * * * *